(12) United States Patent
Brown et al.

(10) Patent No.: US 7,254,501 B1
(45) Date of Patent: Aug. 7, 2007

(54) SPECTRUM SEARCHING METHOD THAT USES NON-CHEMICAL QUALITIES OF THE MEASUREMENT

(75) Inventors: Christopher D. Brown, Albuquerque, NM (US); Gregory H. Vander Rhodes, Melrose, MA (US)

(73) Assignee: Ahura Corporation, Wilmington, MA (US)

( * ) Notice: Subject to any disclaimer, the term of this patent is extended or adjusted under 35 U.S.C. 154(b) by 0 days.

(21) Appl. No.: 11/119,147

(22) Filed: Apr. 30, 2005

Related U.S. Application Data

(60) Provisional application No. 60/635,410, filed on Dec. 10, 2004.

(51) Int. Cl.
*G01R 23/16* (2006.01)
*G01B 3/00* (2006.01)
(52) U.S. Cl. .......................................... 702/76; 702/28
(58) Field of Classification Search ............ 702/22–28, 702/32, 75, 76
See application file for complete search history.

(56) References Cited

U.S. PATENT DOCUMENTS

| 5,850,623 A | * | 12/1998 | Carman et al. ................ 702/28 |
| 6,959,248 B2 | * | 10/2005 | Gard et al. .................... 702/22 |
| 2004/0058386 A1 | * | 3/2004 | Wishart et al. ............... 435/7.1 |

FOREIGN PATENT DOCUMENTS

WO      2006/080939    *   8/2006

OTHER PUBLICATIONS

Lowry, "Automated Spectral Searching In Infrared, Raman And Near-Infrared Spectroscopy", J. Wiley & Sons Ltd., 2002, 1948-1961.
Stauffer et al., "Probability-Based-Matching Algorithm with Forward Searching Capabilities for Matching Unknown Mass Spectra of Mixtures", Anal. Chem. 1985, 57, 1056-1060.
Cleij et al., "Reproducibility As The Basis Of A Similarity Index For Continuous Variables In Straightforward Library Search Methods," Analytica Chimica Acta, 1983, 150, 29-36.
Li et al., "Comparison Of Spectra Using A Bayesian Approach. An Argument Using Oil Spills As An Example", Anal. Chem., 2005, 77, 639-644.

* cited by examiner

*Primary Examiner*—Michael Nghiem
(74) *Attorney, Agent, or Firm*—Pandiscio & Pandiscio

(57) ABSTRACT

A method for determining the most likely composition of a sample, including obtaining data from a sample, wherein the data includes a representation of a measured spectrum; determining the precision state of the representation of the measured spectrum; providing a plurality of library candidates and, for each library candidate, providing data representing each library candidate, wherein the data includes a representation of a library spectrum; determining a representation of the similarity of the sample to each library candidate using (i) the representation of the measured spectrum; (ii) the precision state of the representation of the measured spectrum; and (iii) the representation of the library spectrum for that library candidate; determining the most likely composition of the sample based upon the determined representations of similarity of the sample to each library candidate; and displaying the most likely composition of the sample to a user.

39 Claims, 13 Drawing Sheets

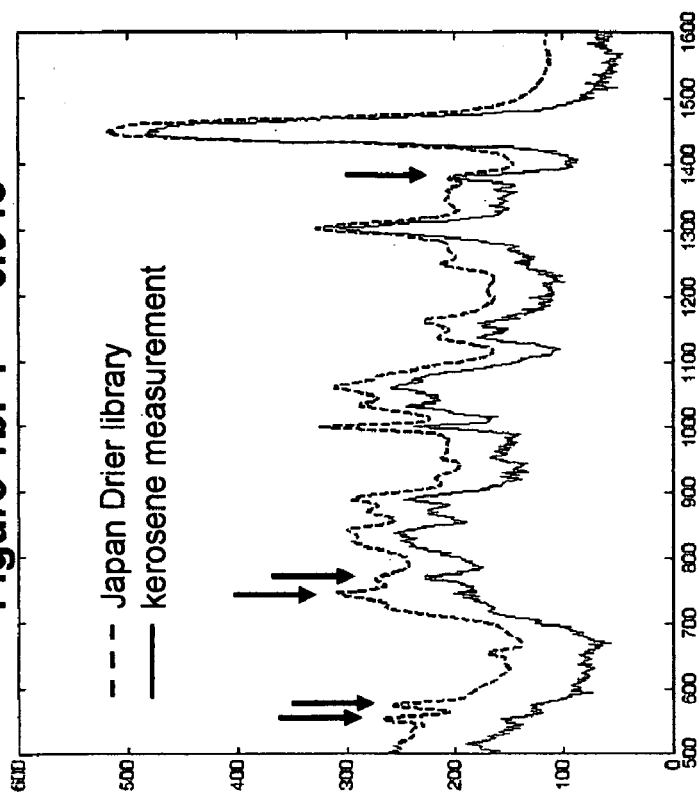
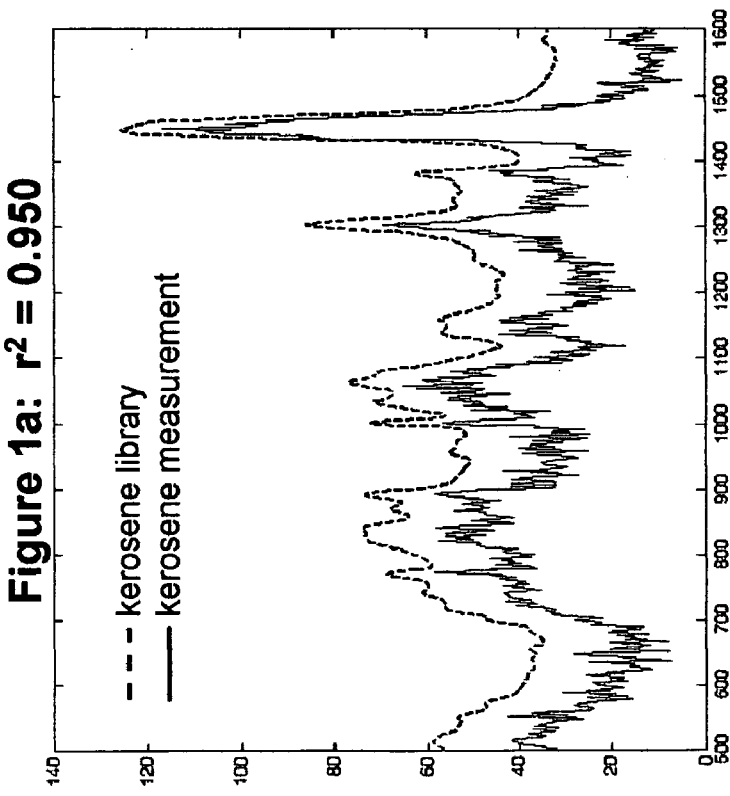

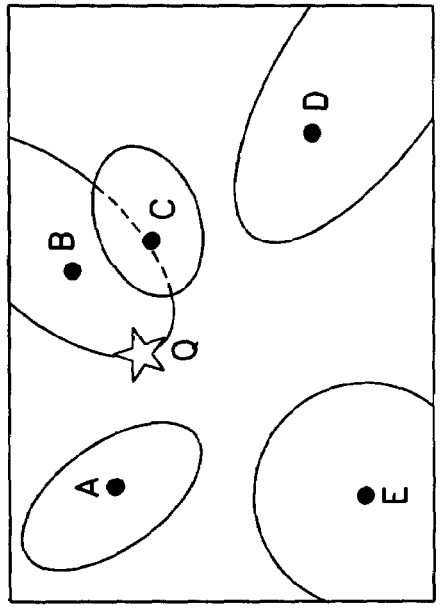
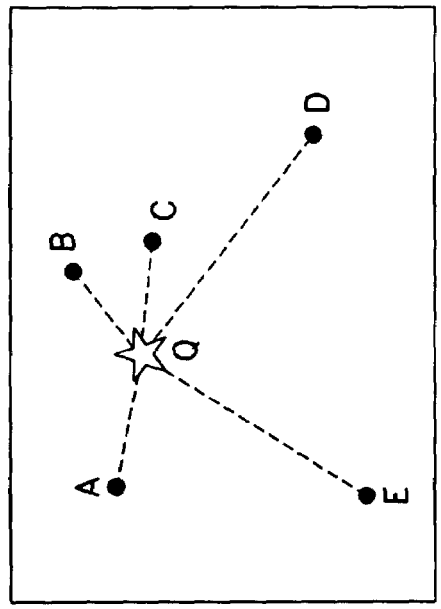
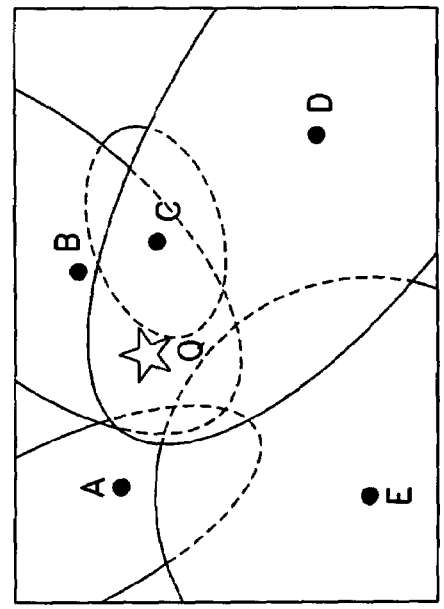

SPECTRUM SEARCHING METHOD THAT USES NON-CHEMICAL QUALITIES OF THE MEASUREMENT

REFERENCE TO PENDING PRIOR PATENT APPLICATIONS

This patent application claims benefit of now abandoned prior U.S. Provisional Patent Application Ser. No. 60/635,410, filed Dec. 10, 2004 by Christopher D. Brown et al. for SPECTRUM SEARCHING METHOD THAT USES NON-CHEMICAL QUALITIES OF THE MEASUREMENT.

The above-identified patent application is hereby incorporated herein by reference.

BACKGROUND OF THE INVENTION

The identification and quantification of chemical entities is largely the domain of analytical chemistry. Both the identification and quantification tasks are made easier with the use of multi-element analytical instrumentation since more analytical information is available to aid the analysis. Examples of contemporary analytical instrumentation capable of producing multi-element (vector) data include multiwavelength infrared and Raman spectrometers, mass spectrometers, nuclear magnetic resonance (NMR) spectrometers, and chromatographic separation-detection systems. Conveniently, as these techniques became more prevalent in the analytical laboratory, computational power also became more affordable and available, and analysts were quick to recognize that computer-aided methods could dramatically speed up the identification and quantification tasks.

In the computer-aided identification task, which is the focus of this patent, the analytical data is submitted to a system (the search appliance) which scours a library of known materials looking for similarities in the instrument response of the unknown material to the stored responses for known materials. Typically, the search appliance returns to the user a list of materials in the library along with their associated similarity to the submitted data. This entire process is usually termed "spectral library searching". The vast majority of proposed similarity measures cannot be interpreted absolutely, but the relative similarity of the measured data to the various library records is deemed meaningful for ranking purposes. This is akin to today's web search utilities that return to the user a list of sites, ordered by a similarity measure of site-to-query. As with web search utilities, the critical differentiation among competing methods is usually the definition of the similarity measure.

The most common similarity measure in use today for spectral library searching is correlation based (see S. R. Lowry, "Automated Spectral Searching In Infrared, Raman And Near-infrared Spectroscopy", J. Wiley & Sons, pp. 1948–1961). This approach exploits a linear instrument response, assuming that a chemical species and its spectrum (InfraRed, Raman, mass spectrum, etc.) are immutably tied, and the vector orientation of the spectrum does not depend on the concentration of the species. Other well-known measures of similarly include Euclidean distance and least-squares methodologies (see S. R. Lowry, "Automated Spectral Searching In Infrared, Raman And Near-Infrared Spectroscopy", J. Wiley & Sons, pp. 1948–1961), which are equivalent to the correlation similarity within elementary scalar manipulations. These similarity measures are implemented in many commercial spectral library search software packages.

In web searching, there are minimal end-user consequences (other than wasted time and frustration) if a page is suggested that does not actually pertain to the query (a "false-positive"). However, many applications of spectral library searching are used to guide actions, such as how chemicals are to be treated in hazardous materials situations, so it is critical to know when an evidence-based decision can be made, and when it cannot. The correlation similarity measure does not suffice to guide actions, as we will illustrate by way example.

FIGS. 1a and 1b illustrate the challenges posed by spectral library search methods using non-absolute similarity measures such as correlation. In both FIGS. 1a and 1b, the measured material is in fact kerosene, a mixture of petroleum distillates in the $C_{12}$ to $C_{15}$ range, but due to different measurement conditions, it is apparent that the precision-states of the two measurements are quite different. In FIG. 1a, the measured kerosene is compared to a library record spectrum of kerosene, yielding a correlation similarity measure of 0.950. In FIG. 1b, the measured kersosene spectrum is compared to a library record spectrum of Japan Drier, a common solvent for painting (a mixture of lighter petroleum distillates), yielding a correlation similarity measure of 0.945. Recall that for any case at hand, the analyst needs to make one of the following judgments based on the similarity measure:

(i) the measured material is likely the top-ranked library material;

(ii) the measured material is likely one of several top-ranked library materials; or (iii) the measured material is not any of the top-ranked materials (i.e., there is no library match).

FIGS. 1a and 1b illustrate the complication in such a decision based on the correlation similarity measure. The different precision states of the two measurements mean that even though the similarity measure is the same in the two cases, one is a valid match (i.e., FIG. 1a), while the other is an invalid match (i.e., FIG. 1b). A simple rule cannot be formulated based on correlation that allows one to reliably decide between judgments (i), (ii) and (iii) above. This is because the correlation similarity measure (and equivalently, least-squares or Euclidean distance measures) does not account for the precision state of the measurement, and therefore does not consistently reflect the amount of scientific evidence favoring a judgment.

Counter-intuitively, when the signal-to-noise ratio is poor, similarity measures in the art tend to more emphatically suggest that the measured material is not in the library; in reality, the evidence provided by the data in such a circumstance is weak—little can be said about whether the material is or is not in the library. Furthermore, when the signal-to-noise ratio increases, the similarity measure tends to increase for all records in the library, when the analyst knows intuitively that with higher quality data, it should be easier to distinguish one library component from another. Indeed, even in FIG. 1b with a very high correlation similarity measure, several obvious mismatched spectral features can be identified (indicated by the arrows in the figure).

What is needed, and to date lacking, in spectral library search algorithms, are similarity measures that are directly interpretable in terms of the scientific evidence supporting one library "hit" over another.

PRIOR ART

Scientific evidence favoring one hypothesis over another is most succinctly quantified in terms of probabilities.

Probabilistic inference is an old and well-explored field, and some allusions to probability-based spectral library searching have been made in the literature.

McLafferty et al. proposed what they termed a probability-based similarity measure for mass spectrum library searching, wherein a small set of features are extracted from the mass spectrum of the query data (such as a list of major peaks and their mass/charge values), they are compared to analogous lists of features in library spectra, and the similarity is made relative to the chance of finding a similar number of matching features at random (see J. R. Chapman, "Computers In Mass Spectrometry", Academic Press, 1978).

Cleij et al. discussed probabilistic similarity measures, wherein selected features of the query spectrum are compared to related features with known uncertainty in the library (see P. Cleij, H. A. Van 'T Klooster, J. C. Van Houwelingen, "Reproducibility As The Basis Of A Similarity Index For Continuous Variables In Straightforward Library Search Methods", Analytica Chimica Acta 150, 23–36, 1983). Their examples include library searches for chemical shift data (NMR spectroscopy), where the uncertainty in the library chemical shift values was determined from measurements at multiple laboratory sites, and chromatographic retention indices where, again, the uncertainty in library retention indices was determined from inter-laboratory variation. There were, however, several critical shortcomings of these investigations.

Neither McLafferty or Cleij discussed methods for comparing complete spectra against alternative library records (often called "full spectrum library searching"), which is the approach of choice today because no information is discarded in the process; neither approach appropriately controls for the increased probability of false-positives associated with multiple tests of hypothesis (typically requiring a Bonferroni-type correction), and, finally, neither approach actually produces posterior probabilities—probabilities of the form, for example, "P is the probability that the material under study is library material A". The McLafferty approach does not account for the uncertainty in the instrumental measurement conditions, and in Cleij's method, the uncertainty in the library record dominates over the uncertainty in the measurement state, which is presumed to be of indisputable quality.

A recent journal article by Li et al. (see J. Li, D. B. Hibbert, S. Fuller, J. Cattle, C. Pang Way, "Comparison Of Spectra Using A Bayesian Approach. An Argument Using Oil Spills As An Example", Anal. Chem. 77, 639–644, 2005) (which in turn claims to build on the work of Killeen and Chien—see T. J. Killeen, Y. T. Chien, "Proc. Workshop Pattern Recognition Appl. Oil Identif.", 1977, pp. 66–72) discussed this general shortfall in spectral library searching, and proposed what they termed a Bayesian approach for spectral matching based on the correlation similarity measure. Their method amounts to a naïve Bayes classifier which has been well-known in the art for some time but, unfortunately, requires measuring many (large multiples of the entire spectral library) specimens, and recording the calculated correlation similarity measures. The distributions of matching and non-matching correlation similarity measures are then used to determine the probability of a match by traditional methods. Even with this procedure, however, the probabilistic assessment is not accurate because the distribution of correlation similarity measures under "no match" criteria only encompasses known species in the library; all other possible species are not represented—so unless the library encompassed "all possible chemical species" (which is practically precluded), the probabilities will be inaccurate. The method they discussed (i.e., a naïve Bayes classifier) also does not adapt to varying measurement conditions.

SUMMARY OF THE INVENTION

The invention disclosed herein resolves these problems, and several related situations that have not be considered in the prior art, for spectral library searching.

In one form of the invention, there is provided a method for determining the most likely composition of a sample, comprising:

obtaining data from a sample, wherein the data comprises a representation of a measured spectrum;

determining the precision state of the representation of the measured spectrum;

providing a plurality of library candidates and, for each library candidate, providing data representing the same, wherein the data comprises a representation of a library spectrum;

determining a representation of the similarity of the sample to each library candidate using (i) the representation of the measured spectrum; (ii) the precision state of the representation of the measured spectrum; and (iii) the representation of the library spectrum for that library candidate; and determining the most likely composition of the sample based upon the determined representations of similarity of the sample to each library candidate.

In another form of the invention, there is provided a method for determining the most likely composition of a sample, comprising:

obtaining data from a sample, wherein the data comprises a representation of a measured spectrum;

determining the precision state of the representation of the measured spectrum;

providing a plurality of library candidates and, for each library candidate, providing data representing the same, wherein the data comprises a representation of a library spectrum;

determining a representation of the similarity of the sample to a mixture of library candidates using (i) the representation of the measured spectrum; (ii) the precision state of the representation of the measured spectrum; and (iii) the representation of the library spectrum for that library candidate; and determining the most likely composition of the sample based upon the determined representations of similarity of the sample to a mixture of library candidates.

In another form of the invention, there is provided a method for determining the most likely classification of a sample, comprising:

obtaining data from a sample, wherein the data comprises a representation of a measured spectrum;

determining the precision state of the representation of the measured spectrum;

providing a plurality of library candidates and, for each library candidate, providing data representing the same, wherein the data comprises a representation of a library spectrum;

wherein the data for each of at least some of the library candidates further comprises the identification of a class to which the library candidate belongs;

determining a representation of the similarity of the sample to each library candidate using (i) the representation of the measured spectrum; (ii) the precision state of the representation of the measured spectrum; and (iii) the representation of the library spectrum for that library candidate; and determining the most likely classification of the sample based upon the determined representations of similarity of the sample to each library candidate.

In another form of the invention, there is provided a method for determining the most likely classification of a sample, comprising:

obtaining data from a sample, wherein the data comprises a representation of a measured spectrum;

determining the precision state of the representation of the measured spectrum;

providing a plurality of library candidates and, for each library candidate, providing data representing the same, wherein the data comprises a representation of a library spectrum;

wherein the data for each of at least some of the library candidates further comprises the identification of a class to which the library candidate belongs;

determining a representation of the similarity of the sample to a mixture of library candidates using (i) the representation of the measured spectrum; (ii) the precision state of the representation of the measured spectrum; and (iii) the representation of the library spectrum for that library candidate; and determining the most likely classification of the sample based upon the determined representations of similarity of the sample to a mixture of library candidates.

In another form of the invention, there is provided a system for determining the most likely composition of a sample, comprising:

apparatus for obtaining data from a sample, wherein the data comprises a representation of a measured spectrum;

apparatus for determining the precision state of the representation of the measured spectrum;

apparatus for providing a plurality of library candidates and, for each library candidate, providing data representing the same, wherein the data comprises a representation of a library spectrum;

apparatus for determining a representation of the similarity of the sample to each library candidate using (i) the representation of the measured spectrum; (ii) the precision state of the representation of the measured spectrum; and (iii) the representation of the library spectrum for that library candidate; and apparatus for determining the most likely composition of the sample based upon the determined representations of similarity of the sample to each library candidate.

In another form of the invention, there is provided a system for determining the most likely composition of a sample, comprising:

apparatus for obtaining data from a sample, wherein the data comprises a representation of a measured spectrum;

apparatus for determining the precision state of the representation of the measured spectrum;

apparatus for providing a plurality of library candidates and, for each library candidate, providing data representing the same, wherein the data comprises a representation of a library spectrum;

apparatus for determining a representation of the similarity of the sample to a mixture of library candidates using (i) the representation of the measured spectrum; (ii) the precision state of the representation of the measured spectrum; and (iii) the representation of the library spectrum for that library candidate; and apparatus for determining the most likely composition of the sample based upon the determined representations of similarity of the sample to a mixture of library candidates.

In another form of the invention, there is provided a system for determining the most likely classification of a sample, comprising:

apparatus for obtaining data from a sample, wherein the data comprises a representation of a measured spectrum;

apparatus for determining the precision state of the representation of the measured spectrum;

apparatus for providing a plurality of library candidates and, for each library candidate, providing data representing the same, wherein the data comprises a representation of a library spectrum;

wherein the data for each of at least some of the library candidates further comprises the identification of a class to which the library candidate belongs;

apparatus for determining a representation of the similarity of the sample to a mixture of library candidates using (i) the representation of the measured spectrum; (ii) the precision state of the representation of the measured spectrum; and (iii) the representation of the library spectrum for that library candidate; and apparatus for determining the most likely classification of the sample based upon the determined representations of similarity of the sample to a mixture of library candidates.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 1$a$ is a view showing a spectral comparison between a kerosene measurement and a kerosene library record;

FIG. 1$b$ is a view showing a spectral comparison between a kerosene measurement and a Japan Drier library record;

FIG. 2: panel 1 is a view showing the similarity measure for a query Q and library records A–E, where both the query and library records are treated as points FIG. 2: panel 2 is a view showing the similarity measure for a query Q and library records A–E, where the query is treated as a point and the candidate library records are treated as ellipses to represent the expected variability in measurement of the materials A–E;

FIG. 2: panel 3 is a view like that of FIG. 2: panel 2 except that there is considerable uncertainty in the expected variability in measurement of the materials A–E;

FIG. 3$b$ is the dark field count, bright field count and Raman spectrum for acetaminophen where there is little background flux;

DETAILED DESCRIPTION OF THE PREFERRED EMBODIMENTS

Figure 3A:
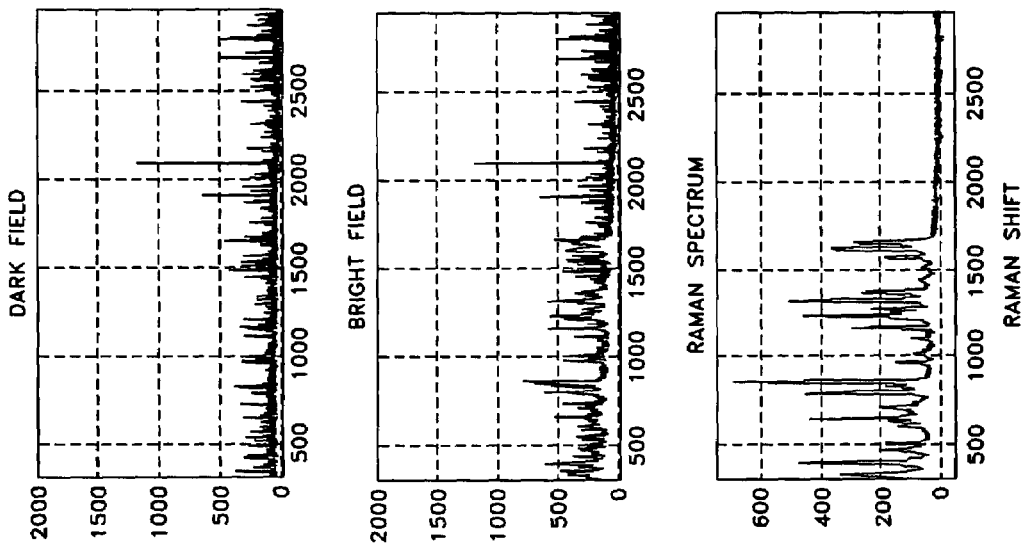
FIG. 3$a$ is the dark field count, bright field count and Raman spectrum for acetaminophen where there is substantial broadband background flux.

The critical question to be answered by the spectral library search appliance is: given the instrumental measurement of the specimen, and the conditions under which it was measured, (1) is it probable that any of the library records are a match?, and (2) what are the probabilities PA, PB . . . that the measured material is in fact pure A, B, etc.? These probabilities must be directly dependent on the measurement data, and its quality. Generally speaking, the measurement quality is a function of the accuracy of the measurement and its precision (or variability). It can often be assumed that, if the instrument has been designed appropriately and/or appropriate signal conditioning methods have been used, the measurement will be reasonably accurate, but inevitably suffers from imprecision to a degree dependent on the measurement conditions.

The inventiveness of the new approach discussed herein, relative to prior art, is most generally described as:

$$S_i = f(y_{lib,i}, y_{meas}, \Sigma_i, \Sigma_{meas}, \Psi) \quad (1)$$

where $S_i$ is the similarity measure between (i) the ith library spectrum, $y_{lib,i}$, for a given library material 1, and (ii) the measured spectrum $y_{meas}$. For the new approach of the present invention, the similarity metric is conditional on $\Sigma_i$, $\Sigma_{meas}$, which are representations of the "precision state" of the library ($\Sigma_i$) and the measured spectrum ($\Sigma_{meas}$) under the circumstances, and $\Psi$ codifies other information available at the time of the similarity analysis.

By direct comparison, conventional spectral library search methods of the sort known to those skilled in the art are best described as:

$$S_i = f(y_{lib,i}, y_{meas}) \quad (2)$$

Certainly $y_{meas}$ will be a consequence of the measurement circumstances—for example, if the circumstance leads to either particularly low signal, or high noise conditions, $y_{meas}$ will "look noisy"—and for this reason, it is sometimes (falsely) suggested that the conventional method of Equation (2) automatically accounts for the precision state. The difference between the new method of Equation (1) and the conventional method of Equation (2) is that the new method of Equation (1) separately quantifies the degree of imprecision in the data to provide the similarity measure that is a direct measure of probabilistic evidence.

The contrast between an evidence-based similarity measure and what is conventionally used in the art is illustrated in FIG. 2. In panel 1 the measurement, treated as a query (Q) for the search appliance, is assessed for similarity to 5 candidate library records (A–E). In panel 1, both the query and library records are treated as points (like the method of equation 2 above), and their similarity (Q to A, Q to B, etc.) is usually a simple function of the distance between points. By this rule, the similarity metrics of Q to A, B, and C are comparable. In panel 2, the measurement query is assumed to be imprecise, and the ellipses around the candidate library records A–E represent the expected variability (e.g., 99%) in measurements of the various materials (A–E) under the precision state of the query. In this case, library record B is the only library record that has a reasonable likelihood of generating the query data given the precision state (although even this is somewhat improbable given the ellipse). Panel 3 reflects a measurement condition in which there is considerable uncertainty (e.g., strong sample fluorescence, which contributes substantial noise to the measurement). The precision state of the query is such that library records B, C and D are all reasonably plausible, although records A and E are less likely. The precision-state-based similarity metric is higher for all 5 library records in panel 3 compared to panel 2, because there is greater uncertainty in the measurement. In the limit, if the imprecision was near infinite (that is, there is very little signal relative to the noise), all library records would be plausible matches, because there is very little (if any) evidence from the measurement to favor one over the other.

One skilled in the art will recognize that there are many possible embodiments of a precision-state-based similarity measure, but all of these embodiments will be critically reliant on a method of characterizing the precision-state of the measurement. For a dispersive Raman spectrometer measurement using charge coupled device (CCD) detection, as an example, many distinct sources of variability contribute to the precision state of the measurement:

$$\Sigma_{meas} = f(I_{Ral}, I_{Ram}, I_{fl}, I_{ambient}, I_{dark}, \sigma_{read}, Q, D_{CCD}, G_{CCD}, C, T, H, t, L) \quad (3)$$

$I_{Ral}$ is the Raleigh scatter intensity, $I_{Ram}$ is the Raman scatter intensity, $I_{fl}$ is the fluorescence intensity, and $I_{ambient}$ is the ambient light intensity. All of these terms affect the uncertainty of the analytical measurement because they each contribute photon shot noise. $I_{dark}$ is the dark current intensity in the CCD, the spontaneous accumulation of detector counts without impinging photons, which also contributes shot noise. $\sigma_{read}$ is the read noise (imprecision in reading out the CCD response), Q is quantization error (a consequence of the analog-to-digital conversion ADC), $D_{CCD}$ is a term relating to variability that is a consequence of defects in the CCD construction, $G_{CCD}$ is the gain on the CCD (the conversion factor from electrons to counts), T and H are the temperature and humidity conditions of the measurement, t is the time spent integrating the signals, C is physicochemical effects that can alter the exact Raman intensities of the sample (note that each of these effects has a potential wavelength dependence), and L is a "long-term" variability term that reflects changes in the system performance over a time period greater than that of any individual sample measurement, e.g., calibration related variability. As is apparent from the above discussion, some sources of imprecision are determined by the measurement conditions (e.g., photon shot noise, dark noise), some are determined by the unit taking the measurements (e.g., system gain, read noise, quantization noise), and some are determined by the overall design of the platform (e.g., wavelength axis and linewidth stability, temperature/humidity sensitivity).

Many of the sources of variability in library spectra are similar, although since library spectra are often desired to be of very high quality, signal averaging can effectively reduce the magnitude of these variances.

There are at least two routes for determining the functional relationship between the measurement parameters and the corresponding precision state: empirical observation and analytical estimation. There are also foreseeable circumstances in which the precision state of the measurement can be inferred from experience, e.g., a measurement being made under very bright ambient lighting conditions will be less precise than a measurement of the same material made in a dark room.

Furthermore, the precision state may be determined by a combination of two or more of empirical observation, analytical estimation and experience.

In empirical observation, many measurements are acquired under a set of conditions, and the imprecision observed over the measurements is characterized using, for example, a variance-covariance matrix. Further, the dependence of such a variance-covariance matrix on other factors can be discerned by focused studies. However, this is rather cumbersome and time-consuming, particularly if rapid similarity judgments are desired and the precision state can vary (as in Raman spectroscopy, FTIR and similar techniques). In many measurement modalities (including Raman, FTIR and other spectroscopies), much about the precision state can often be inferred directly from the properties of the device and/or the environment in which the measurement was acquired. In Raman spectroscopy, for example, read noise and quantization noise are solely functions of the instrument electronics, which are usually fixed for a given spectrometer, and constant across CCD pixels. The total shot noise at a given pixel is dependent on the total counts from all sources registered at that pixel, the gain on the CCD electronics, and a defect factor of that pixel. The temperature and humidity conditions can be determined by on-board transducers, the integration time is known, and the L term can be predetermined from the statistical properties of the system calibration, and its behavior over accelerated life testing. The precision state can change dramatically, however, if the measurement is acquired under different circumstances. For example, a measurement acquired outdoors in bright diffuse sunlight versus a dimly lit room; a meat-storage freezer versus an uncooled storage building; a 0.5 second measurement versus a 5 second measurement.

In FTIR spectroscopy the precision state is also contingent on the measurement conditions, and instrumental aspects such as the detector attributes, data acquisition/signal processing electronics and software, and source flux and flicker.

Figure 3B:
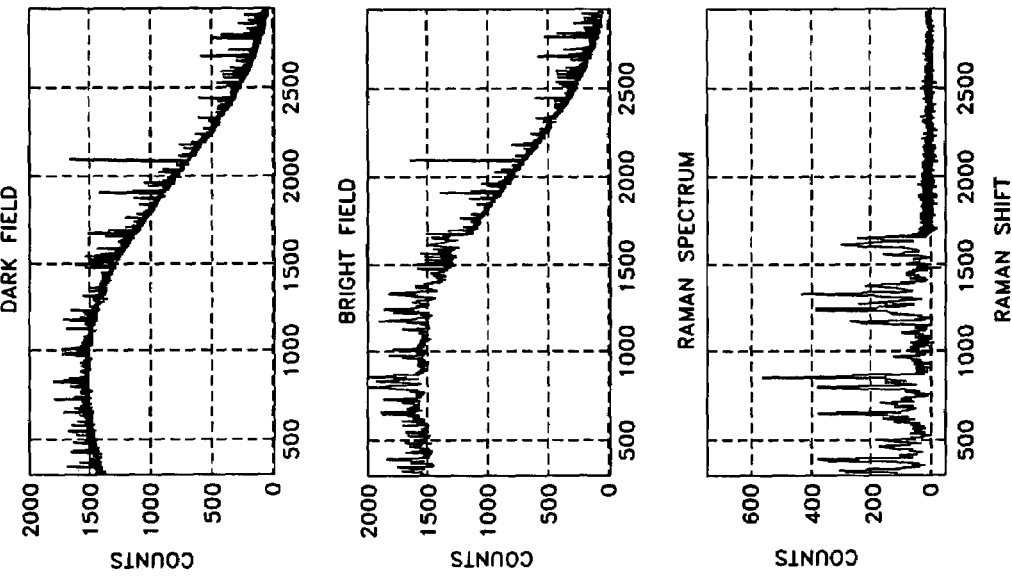

To give an example of the analytical determination of precision state under two different measurement conditions, we show data from a Raman spectrometer in FIGS. 3a and 3b. Both measurements are of acetaminophen in a Raman inactive container for similar exposure times (8 seconds). In FIG. 3a there is sizable broadband background flux from outdoor light pollution evident in both the dark and bright field spectra, while in FIG. 3b there is little background flux. So-called "hot-pixels" are evident in both FIG. 3a and FIG. 3b. The net result, after the usual elementary signal processing operations, are the Raman spectra at the bottom of FIG. 3a and FIG. 3b. The precision-state of these two measurements can be determined at each individual channel as:

$\sigma_{shot}^2$=(total counts dark+total counts bright)/G {G is the effective gain in counts/e⁻, which is impacted by the ADC as well as defects in the pixel}

$\sigma_{total}^2 = \sigma_{shot}^2 = 2*\sigma_{read}^2 + 2*\sigma_{jn}^2$ {read, Johnson and flicker noise}

Figure 4B:
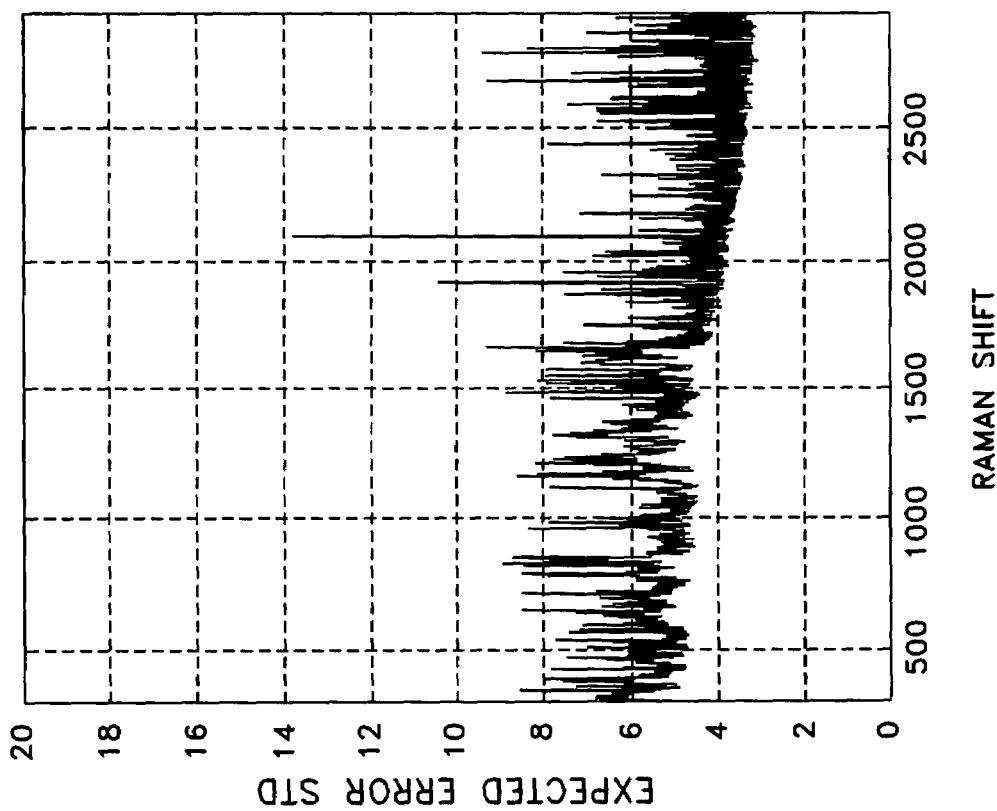
FIGS. 4$a$ and 4$b$ are the analytically estimated standard deviation for each measurement channel for the Raman spectrum for acetaminophen.
Figure 4A:
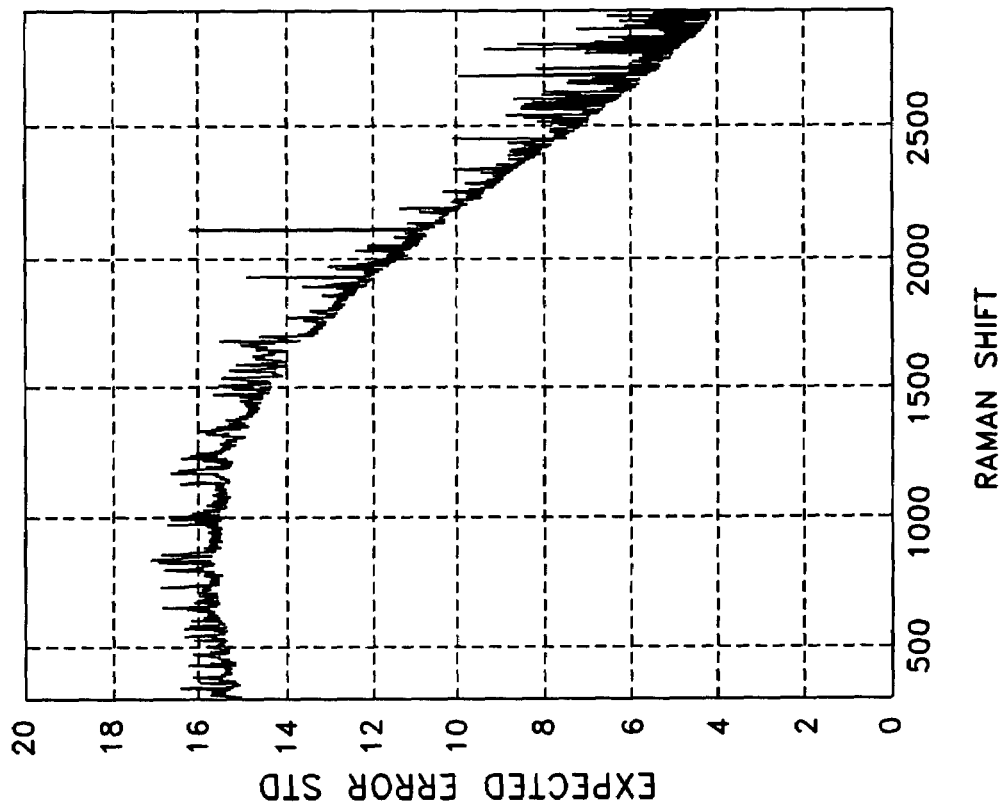

Thus a variance can be determined for each channel of measurement data. There is an excess of shot noise in FIG. 3a because of the background flux, so while the Raman measurements in FIG. 3a and FIG. 3b look similar in terms of signal, FIG. 3a has higher noise due to the ambient shot noise. The precision states are markedly different in these two common cases, as shown in FIGS. 4a and 4b, where the analytically estimated standard deviation at each measurement channel is plotted.

The two cases above were measured on the same system under different ambient conditions, but a similar comparison could have been made on two different systems under the same conditions. The differences in precision states in such a case will be a consequence of the system collection efficiencies, filter/detector responses, as well as the characteristics of the electronics, and ADC. Moreover, in comparing multiple systems under the same measurement conditions, other sources of imprecision will be evident, such as subtle variations in lineshape between systems, wavelength calibration settings, system throughput detector and responsivities. Staying with the variance-covariance representation, these effects generally manifest as covariance terms (off-diagonal non-zero elements in the variance covariance matrix).

Finally, there are physical effects in analytical measurements that can cause distortions in measured data. For example, the Raman scattering intensity at a particular Raman shift value can vary slightly over varying excitation laser wavelengths (leading to slightly different Raman cross-sections), and changes in local polarizability due to solvent and surface effects. In attenuated total reflectance FTIR spectroscopy the refractive index and alignment of the ATR crystal can distort the measured reflectance data. These effects which lead to imprecision across instruments can all be approximated with varying degrees of success using analytic means.

There are other means of representing the precision state of the measurement, for example, Fourier and wavelet-domain representations and reduced-rank representations. The choice of precision-state representation is in large part coupled with a chosen representation of similarity.

Given a representation of the precision state, there are several possible similarity measures that implicitly relate to the scientific evidence favoring library records. For example, in a least-squares formulation, one could assume the model for the system is $$y_{meas} = \beta_0 + \beta_1 \cdot y_{lib,i} + e \quad (4)$$
$$= [1 \quad y_{lib,i}]\begin{bmatrix} \beta_0 \\ \beta_1 \end{bmatrix} + e$$
$$= Y_i \beta + e$$

where $\beta_0$ and $\beta_1$ are constant and multiplicative parameters (assembled into a vector $\beta$), and e is a realization of the variability in the measurement of $y_{lib,i}$, with distribution $e \sim N(0, \Sigma_i)$. One precision-state-based similarity measure can be determined by estimating the generalized lack of fit from the normal equation $$\hat{e}_i = (I_n - Y(Y^T \Sigma_i^{-1} Y)^{-1} Y^T \Sigma_i^{-1}) y_{meas} \quad (5)$$

and then comparing the residual to the expected distribution of e. If $\hat{e}_i$ is not anticipated from the expected distribution of e, then a match is highly improbable. The probability itself is dependent on the distribution of e. If it is multivariate normal, as is the assumption in the case illustrated above, the probability (L) of $\hat{e}$ given $e \sim N(0, \Sigma_i)$ is $$L_i = \frac{\exp\left(-\frac{1}{2}\hat{e}_i^T \Sigma_i^{-1} \hat{e}_i\right)}{\sqrt{(2\pi)^n |\Sigma_i|}} \quad (6)$$

where n is the number of elements in e, and the enclosure |h| indicates the determinant. For very large n, this formula can be challenging to evaluate, so any of a number of numerically efficient alternatives can be exploited, For instance, one can take advantage of the fact that part of the numerator, $\hat{e}_i^T \Sigma_i^T \hat{e}_i$, is $\chi^2$ with n degrees of freedom. To determine the precision-state-based similarity metric, then, one could determine the probability of seeing instantiations of e more extreme than the measurement at hand, the cumulative probability from $\hat{e}_i^T \Sigma_i^{-1} \hat{e}_i$ to $\infty$ on the $\chi^2$ distribution. If the cumulative probability is very low, then if the material represented by the query data is really the same material represented by the library record, it is a very unusual occurrence. Higher probabilities are indicative of much more likely measurements. One skilled in the art will recognize that the precision of various types of instrumentation may be more appropriately characterized by different density functions, such as log-normal, Poisson, or inverse-Gaussian. In these cases the appropriate density function is used to determine the $L_i$ values.

In situations in which the exact distribution of e is approximated empirically rather than being analytically determined, other well-known statistical approximations can be used. For example, empirically estimated normal densities are often characterized using the Wishart distribution, and the chi-squared analog is represented by Snedecor's F-distribution. If the distributional form of e is not known, or cannot be easily parametrically described, empirical cumulative density functions (estimated by, for example, the Kaplan-Meier method—see Cox, D. R. and D. Oakes, "Analysis Of Survival Data", Chapman & Hall, London, 1984) can be used to determine $L_i$. Non-parametric analogs can also be used.

The least-squares formulation above provides a convenient route to a precision-based similarity metric in some circumstances, but other preferred embodiments include a correlation-based similarity measure, where the correlation measure is explicitly adjusted for the precision-state. Discriminant functional representations, neural network architectures, and support vector machines are also all capable of being modified to produce similarity measures that are conditional on the precision-state of the measurement.

In one embodiment, the $L_i$ values are used as measures of precision-state-based similarity. Alternatively, or as a continuation of this embodiment, with a series of $L_i$'s calculated for multiple library spectra, one can determine the exclusive probability that the measured material is a pure representation of one library entry versus another, often termed the "posterior probability". Bayes theorem gives the posterior probability, $P_i$, (exclusive) for a given library component:

$$P_i = \frac{\theta_i L_i}{\sum_{j=1}^{k} \theta_j L_j} \quad (7)$$

where there are k elements in the library, or k elements under consideration. The symbol $\theta$ codifies other information regarding a given library component independent of the instrument measurement under the constraint that the sum of all $\theta$ values must equal 1 (an aspect of $\Psi$ discussed above). For a simple example, consider the case where the analyst knows the unknown specimen of interest is a white powder. Some of the library records may be associated with materials that are white powders in pure form. Therefore, the $\theta$ values for each library entry can be chosen to reflect the fact that white-powder library materials are more probabilistically likely than non-white-powder materials. There is an important distinction between what is commonly done by those practicing the art—which is to exclude from the search library records which do not correspond to white powders—and the above approach, which quantitatively reflects probabilities and comprises the other novel aspect of the disclosed spectral library search method. We detail this aspect and its utility next.

If no extra (i.e., non-instrument measurement) information is available at the time of the measurement, each $\theta$ is set to 1/k, indicating that no prior preference exists for any particular library component, a condition usually termed a "flat prior" in the probability literature. The evidence-based similarity measure of this embodiment allows for "scenarios" that do make some library species more likely than others, but never with $\theta$=0 or 1. For example, if a white powder is being analyzed (a characterization which is an input from the user), then all library components that could be in white powder form are given preferred prior probability, for example, $\theta$ might favor white-powders over organic liquids 4:1. This is preferred over setting $\theta$ equal to zero for non-white powder substances, because users cannot be completely relied upon for perfect input, and phase changes of materials are possible in different measurement conditions. Further, prior probabilities can never be 0 or 1 in any circumstance (except, perhaps for some pathological cases), because these states convey absolute certainty about the as yet unknown outcome.

Other attributes that can be used to determine the prior probability include, but are not limited to, odor, appearance, texture, crystallinity, color, etc. In these cases, a user can either be prompted for other information (e.g., "What is the color of the substance? Is it solid, liquid?" etc.), or they may choose one or more predefined scenarios that represent one attribute, or a combination of attributes. For example, hazardous materials and drug enforcement personnel often refer to "white powder" scenarios. In this case, the prior probabilities can be automatically set to reflect pre-measurement odds favoring materials in the library that meet these criteria. Therefore, the user could either be presented with the probability $L_i$, which represents the probability that library material i and precision state could lead to the observed measurement, or $P_i$ which is the probability that the material under study is library material i given the precision state and other prior information encoded in the various $\theta_i$ values.

In one embodiment of this invention, the $\theta_i$ values are determined by a multinomial logistic model on physicochemical properties of samples including color, odor, form (e.g., solid, liquid, gas), while in another embodiment the θ values are determined from text searches of a database of material properties with correspondences to the spectral library. In yet another embodiment, the θ's are modified according the "hazardousness" of the library material, which is advantageous in preventing false-negative search results when such errors could be highly dangerous, a risk-based prior probability.

Figure 5:
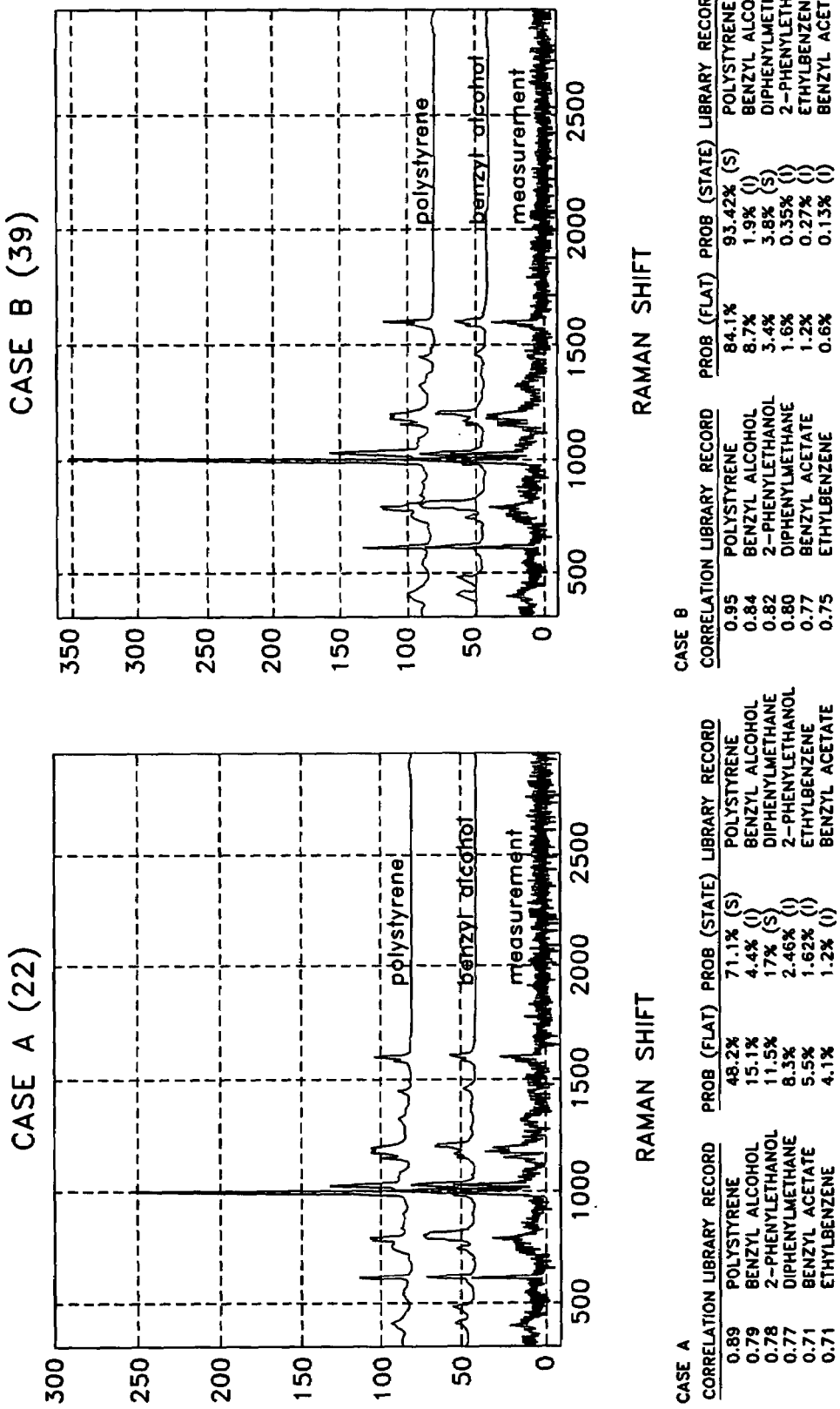
FIG. 5 provides a comparative example of the present invention for two measurements of polystyrene.

FIG. 5 gives a comparative example of this entire process for two measurements of polystyrene. Case A has a relatively low signal-to-noise ratio (SNR), and case B has a slightly better SNR. The tables below the graphs compare (i) a correlation-based search to (ii) an evidence-based approach contingent on the precision state. For the evidence-based search, we also compare search under a flat prior to search using a state-based prior (solid, liquid, gas). Correlation similarities for the top 6 hits are all in excess of 0.7. Use of the precision-state in Case A, however, reveals that a match for polystyrene is probabilistically favored approximately 3:1 over the next best match, and when the state-based prior is used, polystyrene is favored 20:1 over benzyl alcohol. With the SNR improved slightly in Case B, the correlation similarities all increase (although the differences between similarity measures is essentially the same). The evidence-based search is emphatic that polystyrene is favored almost 10:1 over benzyl alcohol, and; with the state-based prior included, this increases to almost 50:1 odds.

Figure 6A:
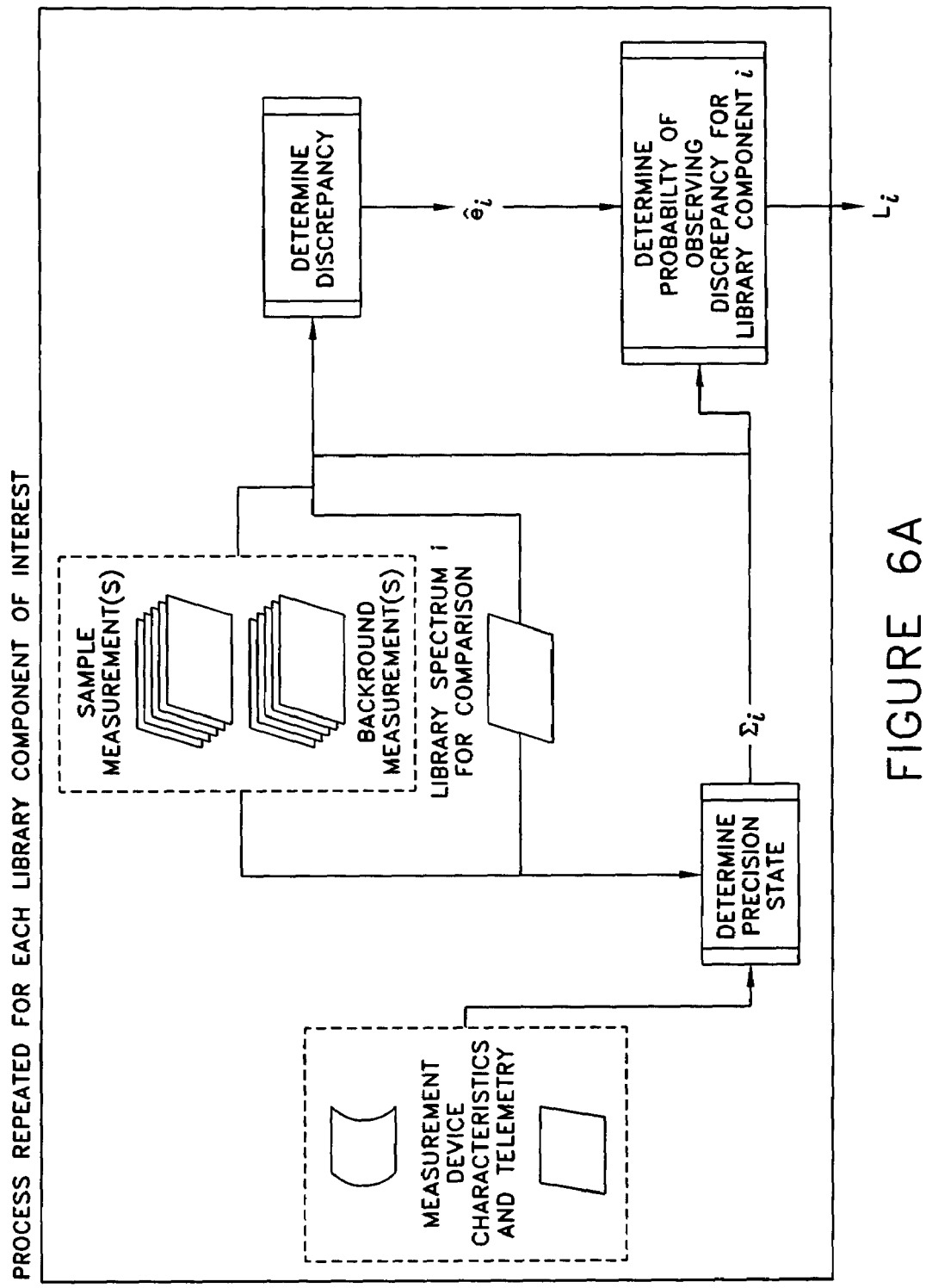
FIG. 6A illustrates the methodology used to determine (i) the discrepancies between a sample measurement and various library records, and (ii) the probability of observing that discrepancy for a particular library record.
Figure 6B:
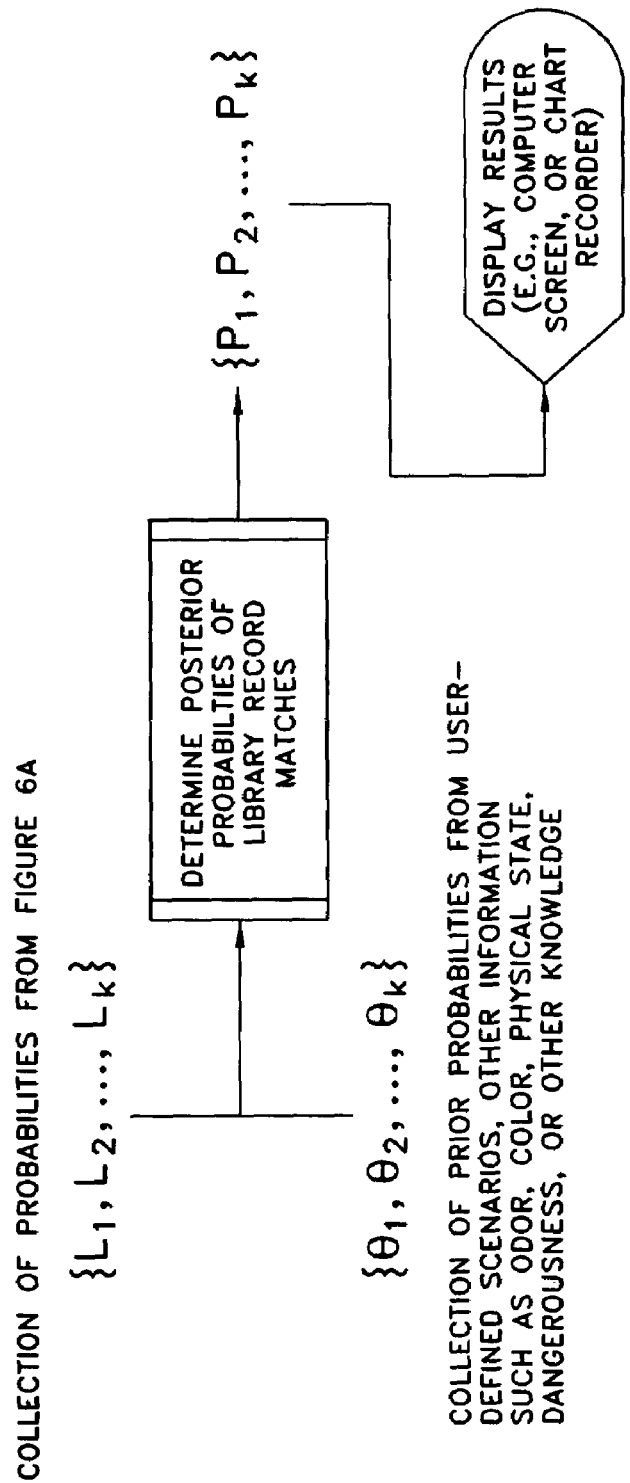
FIG. 6B illustrates the methodology to determine posterior probabilities of library record matches using (i) the calculated probabilities of observing the determined discrepancy for a particular library record, and (ii) the collection of prior probabilities.

FIGS. 6A and 6B illustrate a general embodiment of this novel process.

In some situations it is advantageous to use manipulations of the measurement or library data to improve signal-to-noise ratio, favorably alter the signal character, or compress the data for ease of calculation and storage. Further, for some applications of spectral library searching parametric similarity functions may be difficult to formulate, and instead non-parametric alternatives are advantageously employed, and the measurement data and library data must be represented in a form that is amenable for the non-parametric similarity analysis. Common examples of signal manipulations/compression include Fourier and wavelet filtering, compression by principal components, polynomial smoothing and derivative filters, and spline-based manipulations. Non-parametric manipulations include binary representations of spectrum band positions/heights, tabulated functional values, etc. One skilled in the art will recognize that, in these cases, the representation of the precision-state (e.g., the variance-covariance matrix) must also be manipulated so that it is representative of the precision state of the representation of the measurement data.

Figure 7:
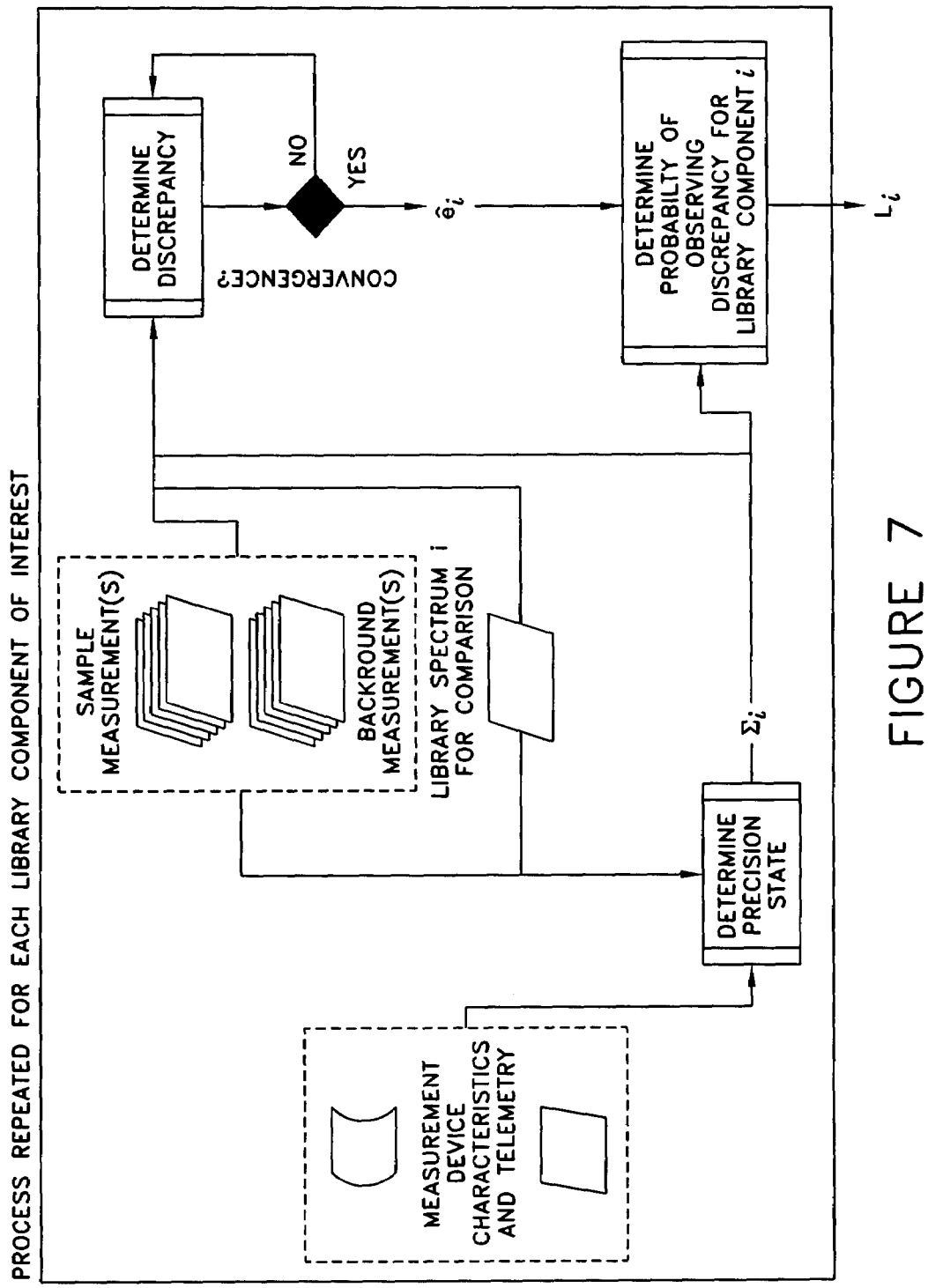
FIG. 7 illustrates the methodology used to determine (i) the discrepancies between a sample measurement and various library records, and (ii) the probability of observing that discrepancy for a particular library record, using a test for convergence.

Some variability terms depend on the magnitude of the library spectrum that most closely matches the measured spectrum. For example, one might examine the probability that a particular library spectrum could give rise to the measurement (the measurement is a random observation from a distribution around the library spectrum), in which case the Raman shot noise will depend on the magnitude of the library spectrum that best describes the measurement. Therefore, the Raman shot term of Σ and the best fit parameters β must be determined simultaneously. This can be solved by any number of means well known in the art, including alternating least-squares (ALS) (see Young, F. W., "Quantitative Analysis Of Qualitative Data", Psychometrika 46, 357–388, 1981), iterative majorization, or nonlinear optimization methods such as Levenberg-Marquardt (see Levenberg, K., "A Method For The Solution Of Certain Problems In Least Squares", Quart. Appl. Math. 2, 164–168, 1944, and Marquardt, D., "An Algorithm For Least-Squares Estimation Of Nonlinear Parameters", SIAM J. Appl. Math. 11, 431–441, 1963), or the simplex method (see J. A. Nelder and R. Mead, "A Simplex Method For Function Minimization", Computer Journal 7, 308–313, 1965). We have used the ALS and iterative majorization approaches and found that convergence is usually achieved in less than 20 iterations. FIG. 7 illustrates an embodiment of this novel subprocess.

Variability in the Measured and Library Spectra

Ideally, the information in the library is known to infinite or extremely high precision, and one assumes that the imprecision of the measurement condition results in a distribution of potential observations around the library spectrum. But, in practice, library spectra are never perfectly determined. This can be problematic for contemporary library search methods, because all presently used approaches assume the library spectrum is known to infinite accuracy. If the signal-to-noise in the measured spectrum is high enough, part of the dissimilarity between a measurement and the library record may in fact be due to the inaccuracy of the library spectrum itself. The remedy for this problem is to define the variability of the library spectrum itself, again either by measurement or first principles or both, and determine the similarity measures under the constraint that some imprecision is expected in the library spectrum itself. One general approach to this is the extension of Equation 5 by Tikhonov regularization:

$$\hat{e}_i = (I_n - Y(Y^T \Sigma_i^{-1} Y - \Sigma_{lib})^{-1} Y^T \Sigma_i^{-1}) y_{meas} \qquad (10)$$

which constrains the solution according to the variability in the library record $\Sigma_{lib}$. One skilled in the art will recognize that a constraint of this form could be implemented by any number of insubstantially different means (such as further correction of a correlation-based measure for the imprecision of the library spectrum), but the critical aspect is that the similarity measures depend on $\Sigma_{lib}$.

Non-Linear Discrepancy Approaches

One skilled in the art will recognize that, while we have illustrated a linear discrepancy analysis approach, the use of variability information in the derivation of a similarity metric for the user could equally apply to non-linear discrepancy estimating methods such as neural networks, support vector machines, nearest-neighbor methods, etc.

Use of Variability to Direct Operation of Measurement Device

Figure 8:
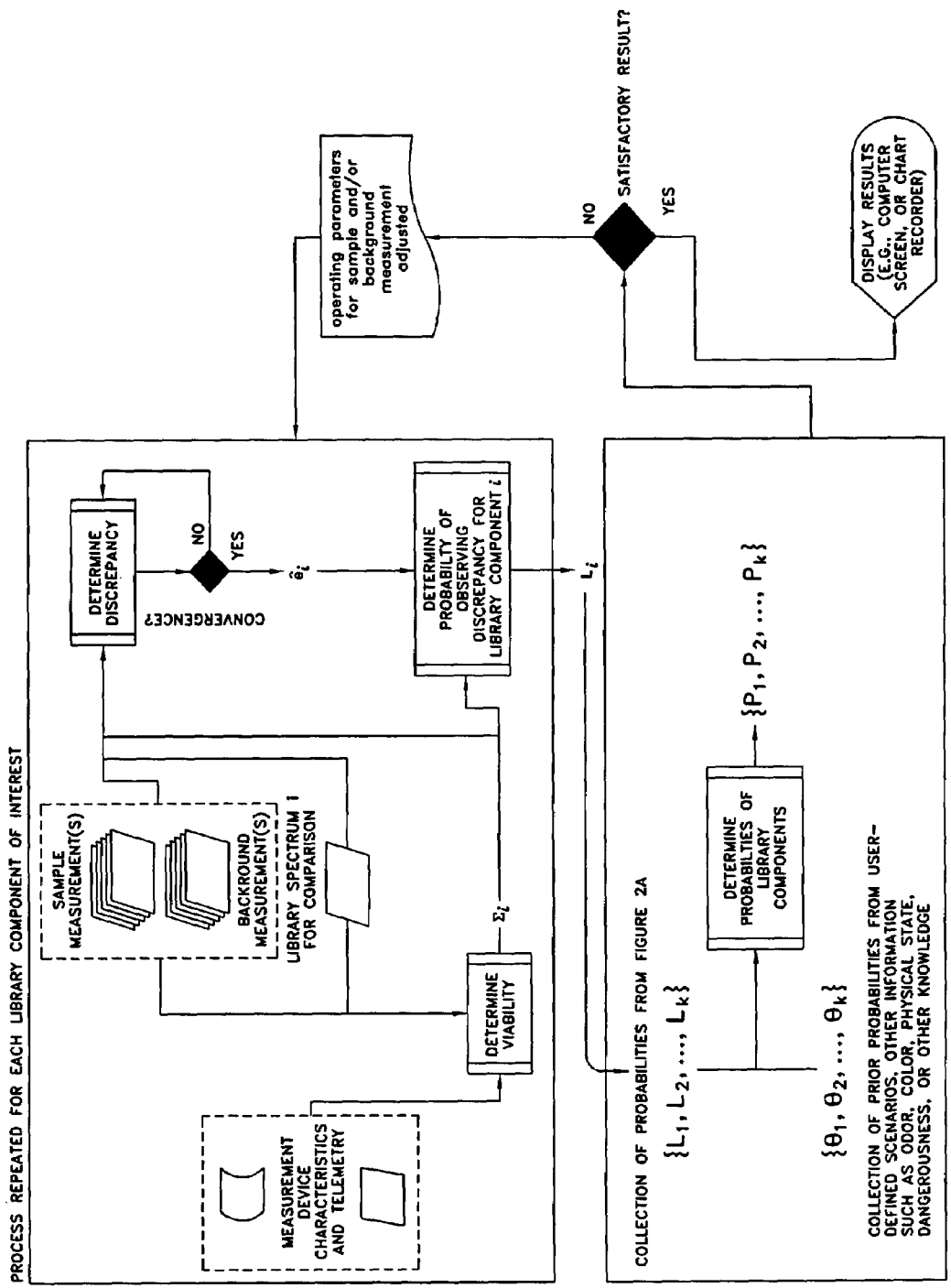
FIG. 8 is a composite of FIGS. 7 and 6B, further modified to show adjustment of operating parameters so as to improve the result.

An aspect of the described invention is to control the operation of a measurement device such that a precision state is achieved that allows for a more definitive assessment of the probable matches, that is, the measurement device is operated such that substantial evidence favors only one or two possibilities. This can be thought of as occurring by forcing non-similar candidates have an even lower similarity measure by altering the conditions of the measurement. Provided that the variability term Σ can be influenced by controllable device operating parameters, such as source intensity, integration time, aperture, resolution, etc., such a device could make a measurement with known operating parameters, determine the precision state of such a measurement, and if the evidence is insufficient to make a sound determination of the composition of the sample in question, alter the device operating parameters in such a way that the precision state is more favorable. FIG. 8 illustrates an embodiment of this approach. Additionally or alternatively, the device could instruct in the user to alter the measurement characteristics in a way that is favorable for the precision state, e.g., 'shield the sample from impinging light pollution', 'reposition the measurement device for more efficient collection', change the device operating characteristics.'

Mixture Extension

The use of variability information to assess the similarity of a measurement to a library component, extends seamlessly to the assessment of the similarity of a measurement to a mixture of library components. Instead of $$Y=[1y_{lib,i}] \quad (11)$$

as in Equations 4, 5 and 10 above, Y is expanded to include possible mixture library components $$Y=[1y_{lib,i} \ y_{lib,j} \ldots y_{lib,q}] \quad (12)$$

The procedures discussed above all apply by simple extension, although now the discrepancy, e, is distributed with terms that depend on the precision of the measurement state contributed by each possible library component. Nonetheless, similarity measures can still be derived that depend on the precision state, and many are simple extensions of the non-mixture similarity measures. For example, the probability determinations discussed above remain valid for mixtures of library records, and the method can provide the user with the probability that the measured sample is a mixture of q library components, rather than the probability the measured sample is a pure library component.

Classification

The use of precision-state information can also be useful if the desire is to identify the class of chemical materials that is similar to the measured sample. One could, for instance, determine the precision-based similarity of the measurement to a number of candidates, and the joint probability for the class of compounds can be used for classification purposes, e.g., "explosives", "non-steroidal anti-inflammatory drugs", "narcotics", etc. This is generally termed classification, rather than identification, as the class of compounds is believed to be indicated by the aggregate similarity of the query to collections of library records with similar properties.

Utility

The above invention is extremely useful for materials identification or classification, as it provides the user with a similarity, or similarities measures, that directly quantify the amount of knowledge that exists at the time of the analysis. Actions that follow the analysis are then directly dependent on the knowledge provided by the method, for example, evacuate the immediate area, clean up material using hazard suits, etc. In many instances the knowledge provided by this approach over current methods is expected to yield dramatic savings in money, time, and human lives.

Various Systems for Analyzing a Specimen

It is possible to embody the present invention in many different constructions. Such constructions will be apparent to those skilled in the art in view of the present disclosure.

Figure 9:
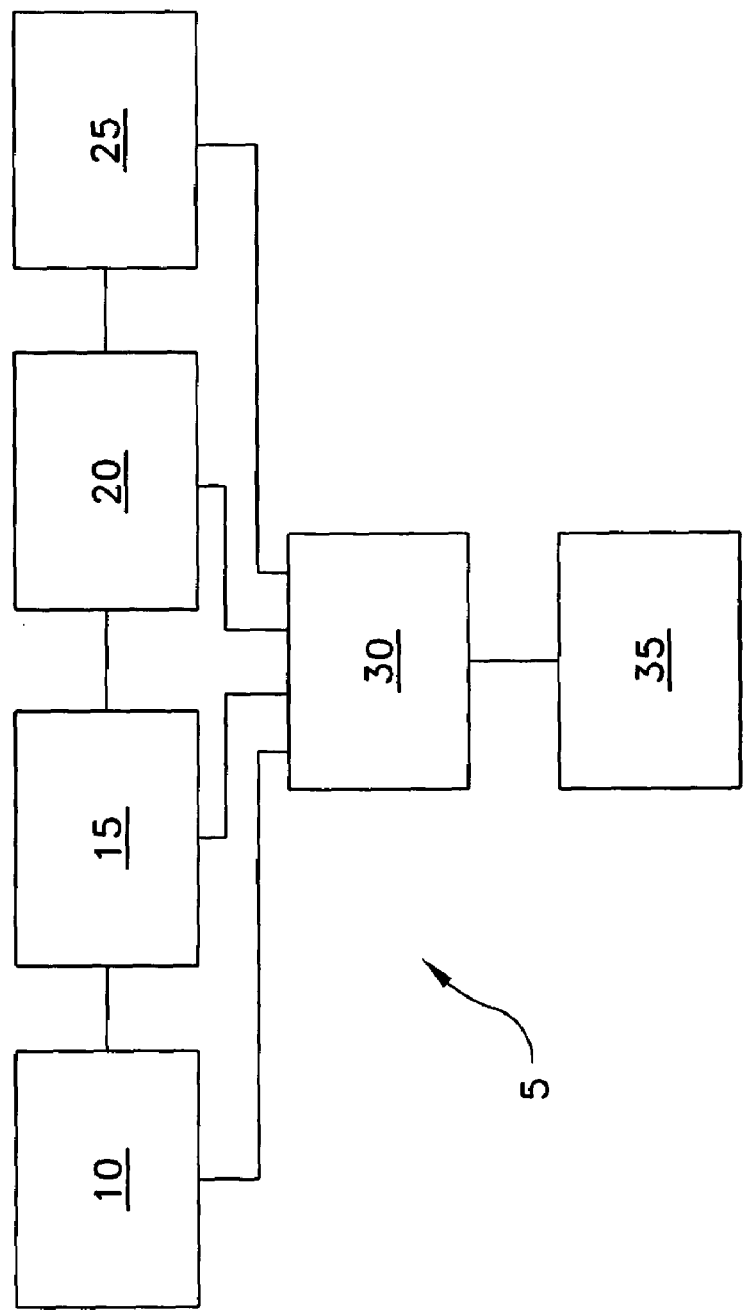
FIG. 9 is a schematic diagram showing one preferred form of apparatus embodying the present invention.

Thus, for example, and looking now at FIG. 9, there is shown a system 5 for determining the most likely composition of a sample, comprising: apparatus 10 for obtaining data from a sample, wherein the data comprises a representation of a measured spectrum; apparatus 15 for determining the precision state of the representation of the measured spectrum; apparatus 20 for providing a plurality of library candidates and, for each library candidate, providing data representing the same, wherein the data comprises a representation of a library spectrum; apparatus 25 for determining the precision state of the representation of each library spectrum; apparatus 30 for determining a representation of the similarity of the sample to each library candidate using (i) the representation of the measured spectrum, (ii) the precision state of the representation of the measured spectrum, (iii) the representation of the library spectrum for that library candidate, and (iv) the precision state of the representation of the library spectrum for that library candidate; and apparatus 35 for determining the most likely composition of the sample based upon the determined representations of similarity of the sample to each library candidate.

Figure 10:
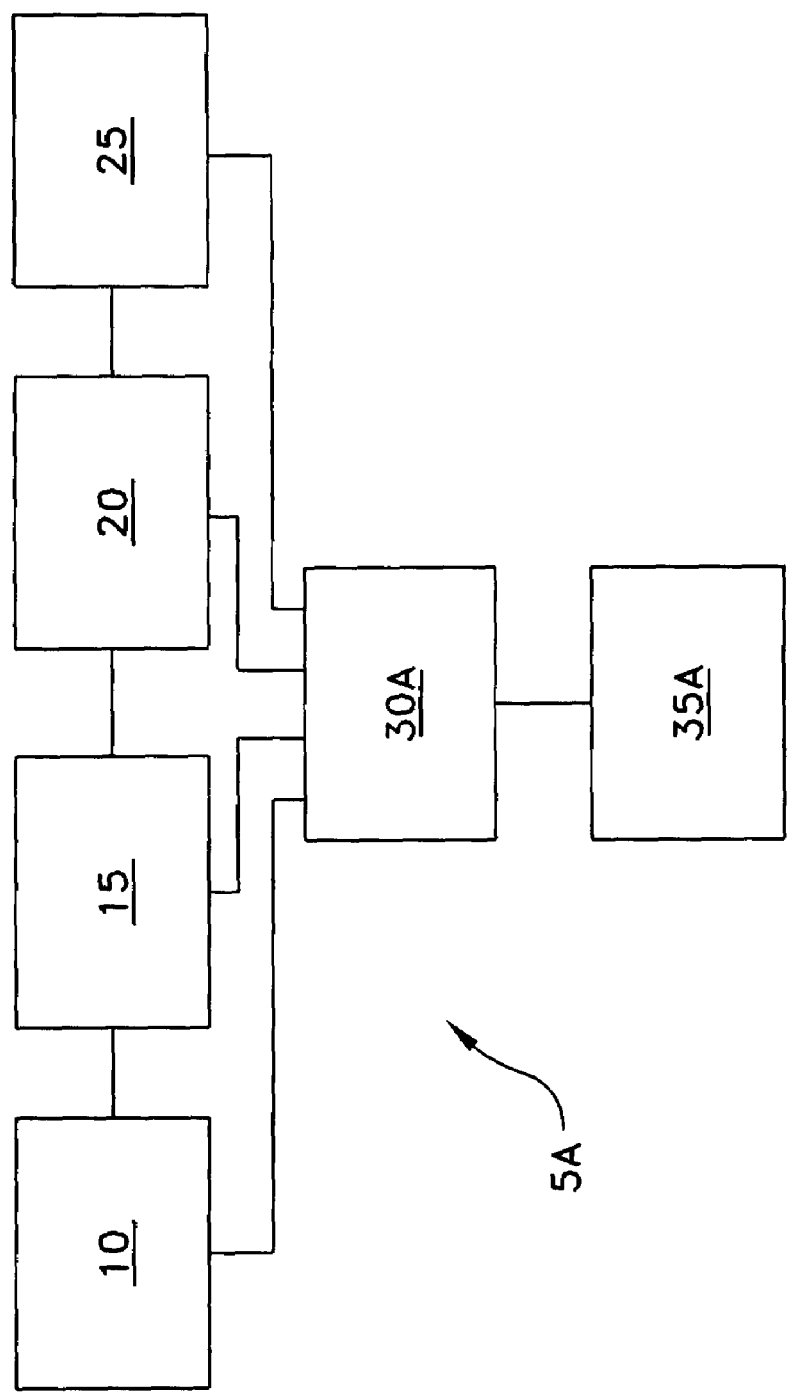
FIG. 10 is a schematic diagram showing another preferred form of apparatus embodying the present invention.

Furthermore, and looking now at FIG. 10, there is shown a system 5A for determining the most likely composition of a sample, comprising:

apparatus 10 for obtaining data from a sample, wherein the data comprises a representation of a measured spectrum; apparatus 15 for determining the precision state of the representation of the measured spectrum; apparatus 20 for providing a plurality of library candidates and, for each library candidate, providing data representing the same, wherein the data comprises a representation of a library spectrum; apparatus 25 for determining the precision state of the representation of each library spectrum; apparatus 30A for determining a representation of the similarity of the sample to a mixture of library candidates using (i) the representation of the measured spectrum, (ii) the precision state of the representation of the measured spectrum, (iii) the representation of the library spectrum for the library candidates, and (iv) the precision state of the representation of the library spectrum for the library candidates; and apparatus 35A for determining the most likely composition of the sample based upon the determined representations of similarity of the sample to a mixture of library candidates.

Figure 11:
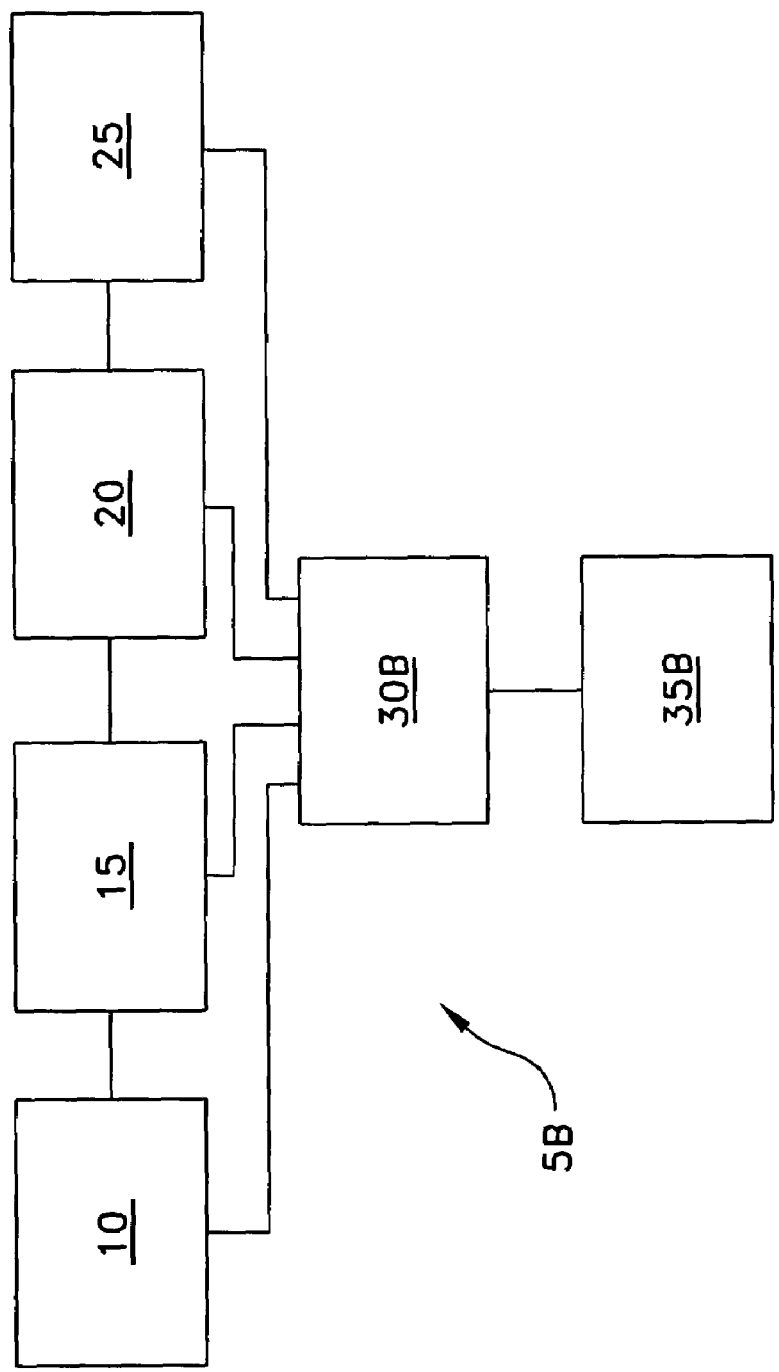
FIG. 11 is a schematic diagram showing another preferred form of apparatus embodying the present invention.

Furthermore, and looking now at FIG. 11, there is shown a system 5B for determining the most likely classification of a sample, comprising: apparatus 10 for obtaining data from a sample, wherein the data comprises a representation of a measured spectrum; apparatus 15 for determining the precision state of the representation of the measured spectrum; apparatus 20 for providing a plurality of library candidates and, for each library candidate, providing data representing the same, wherein the data comprises a representation of a library spectrum; apparatus 25 for determining the precision state of the representation of each library spectrum; wherein the data for each of at least some of the library candidates further comprises the identification of a class to which the library candidate belongs; apparatus 30B for determining a representation of the similarity of the sample to a mixture of library candidates using (i) the representation of the measured spectrum, (ii) the precision state of the representation of the measured spectrum, and (iii) the representation of the library spectrum for that library candidate; and apparatus 35B for determining the most likely classification of the sample based upon the determined representations of similarity of the sample to a mixture of library candidates.

Raman Spectroscopy Applications

It is possible to utilize the present invention in many applications.

It is particularly useful in applications involving Raman spectroscopy.

Figure 12:
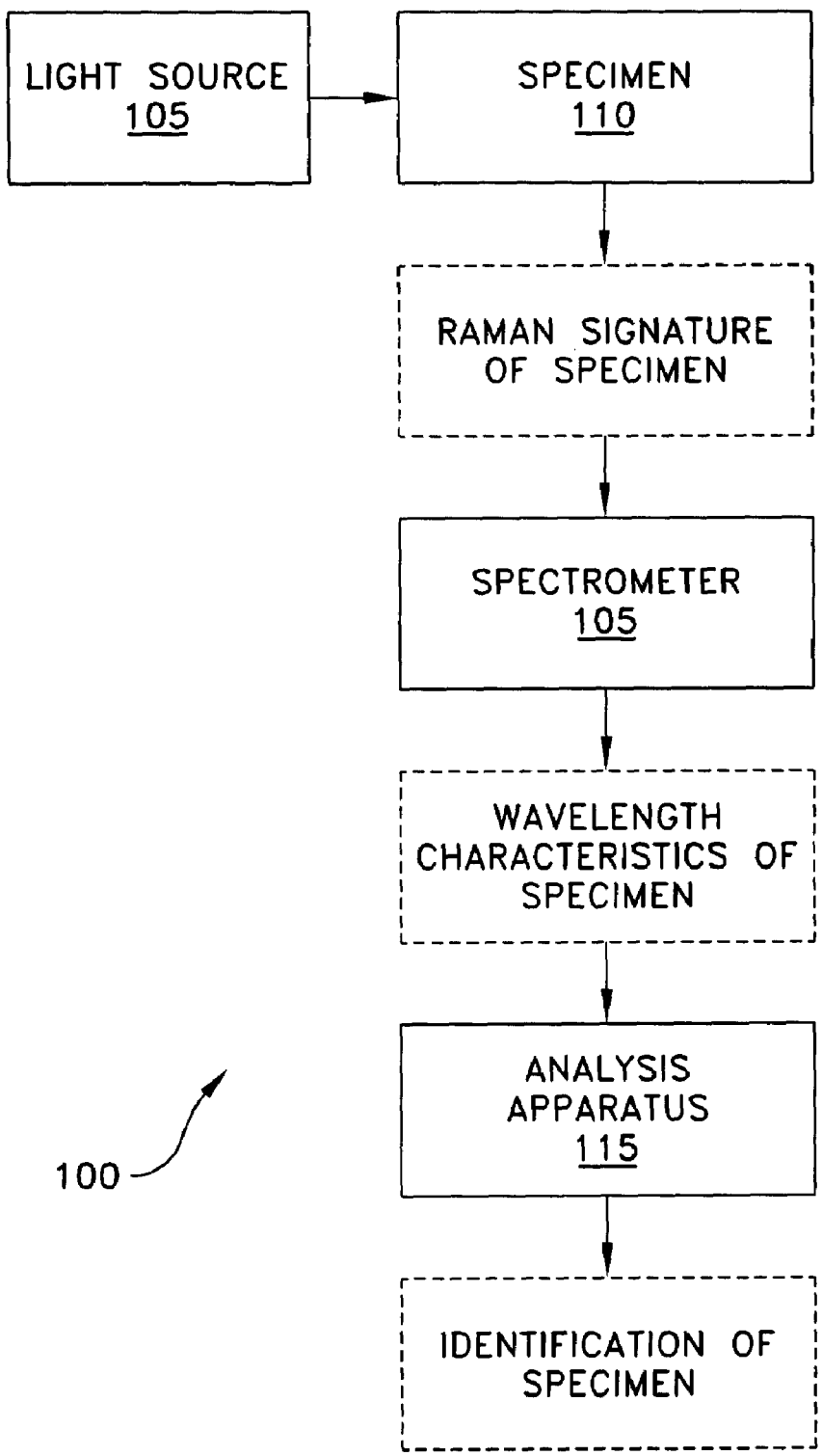
FIG. 12 is a schematic view showing a novel Raman analyzer formed in accordance with the present invention.

Thus, for example, in FIG. 12 there is shown (in schematic form) a novel Raman analyzer 100 formed in accordance with the present invention. Raman analyzer 100 generally comprises an appropriate light source 105 (e.g., a laser) for delivering excitation light to a specimen 110 so as to generate the Raman signature for the specimen being analyzed, a spectrometer 105 for receiving the Raman signature of the specimen and determining the wavelength characteristics of that Raman signature, and analysis apparatus 115 formed in accordance with the present invention for receiving the wavelength information from spectrometer. 105 and, using the same, identifying specimen 110.

FURTHER MODIFICATIONS

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. A method for determining the most likely composition of a sample, comprising:
   obtaining data from a sample, wherein the data comprises a representation of a measured spectrum;
   determining a precision state of the representation of the measured spectrum;
   providing a plurality of library candidates and, for each library candidate, providing data representing each library candidate, wherein the data comprises a representation of a library spectrum;
   determining a representation of the similarity of the sample to each library candidate using (i) the representation of the measured spectrum; (ii) the precision state of the representation of the measured spectrum; and (iii) the representation of the library spectrum for that library candidate;
   determining the most likely composition of the sample based upon the determined representation of similarity of the sample to each library candidate; and
   displaying the most likely composition of the sample to a user.

2. A method according to claim 1 wherein the method further comprises:
   determining the precision state of the representation of each library spectrum; and
   determining a representation of the similarity of the sample to each library candidate using (i) the representation of the measured spectrum; (ii) the precision state of the representation of the measured spectrum; (iii) the representation of the library spectrum for that library candidate; and (iv) the precision state of the representation of the library spectrum for that library candidate.

3. A method for changing the operating characteristics of a measurement device, based on a representation of the measurement of a sample, comprising:
   the method according to claim 2, and further comprising:
   determining the precision state of the representation of the measurement;
   determining a quantity related to the determined representation of similarity of the sample to each library candidate; and
   changing the operating characteristics of the measurement device such that the similarity of a different measurement acquired with the changed operating characteristics to one or more candidates is reduced.

4. A method according to claim 1 wherein a precision state is determined by empirical observation.

5. A method according to claim 4 wherein a determined precision state is represented using a variance-covariance matrix.

6. A method according to claim 4 wherein a determined precision state is represented using the Wishart distribution.

7. A method according to claim 4 wherein a determined precision state is represented using the Snedecor's F-distribution.

8. A method according to claim 4 wherein a determined precision state is represented using empirical cumulative density functions.

9. A method according to claim 1 wherein a precision state is determined by analytical estimation.

10. A method according to claim 1 wherein a precision state is determined by experience.

11. A method according to claim 1 wherein a precision state is determined by a combination of two or more from the group consisting of empirical observation, analytical estimation and experience.

12. A method according to claim 1 wherein the determination of a precision state incorporates environmental factors.

13. A method according to claim 1 wherein the determination of a precision state incorporates device characteristics.

14. A method according to claim 1 wherein the method is implemented using a digital computer system.

15. A method according to claim 1 wherein the method is implemented using a computer program stored on a computer-readable medium.

16. A method according to claim 1 wherein:
   the data from the sample further comprises a least one observed property of the sample;
   the data for each of at least some of the library candidates further comprises a least one observed property of the library candidate; and
   the representation of the similarity of the sample to each library candidate is determined using (i) the representation of the measured spectrum; (ii) the precision state of the representation of the measured spectrum; (iii) the representation of the library spectrum for that library candidate; (iv) the at least one observed property of the sample; and (v) the a least one observed property for that library candidate to the extent that there is an observed property for that library candidate.

17. A method according to claim 16 wherein the method further comprises:
   determining the precision state of the representation of each library spectrum; and
   the representation of the similarity of the sample to each library candidate is determined using (i) the representation of the measured spectrum; (ii) the precision state of the representation of the measured spectrum; (iii) the representation of the library spectrum for that library candidate; (vi) the precision state of the representation of the library spectrum for that library candidate;

(v) the at least one observed property of the sample; and (vi) the a least one observed property for that library candidate to the extent that there is an observed property for that library candidate.

18. A method for changing the operating characteristics of a measurement device, based on a representation of the measurement of a sample, comprising:

the method according to claim 16, and further comprising:

determining the precision state of the representation of the measurement;

determining a quantity related to the determined representation of similarity of the sample to each library candidate; and changing the operating characteristics of the measurement device such that the similarity of a different measurement acquired with the changed operating characteristics to one or more candidates is reduced.

19. A method according to claim 1 wherein:

the data from the sample further comprises a least one observed property of the sample;

the data for each of at least some of the library candidates further comprises a least one observed property of the library candidate and a prior probability associated with that observed property of the library candidate; and the representation of the similarity of the sample to each library candidate is determined using (i) the representation of the measured spectrum; (ii) the precision state of the representation of the measured spectrum; (iii) the representation of the library spectrum for that library candidate; (iv) the at least one observed property of the sample; (v) the a least one observed property for that library candidate to the extent that there is an observed property for that library candidate; and (vi) the prior probability associated with that observed property of the library candidate.

20. A method according to claim 19 wherein the method further comprises:

determining the precision state of the representation of each library spectrum; and the representation of the similarity of the sample to each library candidate is determined using (i) the representation of the measured spectrum; (ii) the precision state of the representation of the measured spectrum; (iii) the representation of the library spectrum for that library candidate; (iv) the precision state of the representation of the library spectrum for that library candidate;

(v) the at least one observed property of the sample; (vi) the a least one observed property for that library candidate to the extent that there is an observed property for that library candidate; and (vii) the prior probability associated with that observed property of the library candidate.

21. A method according to claim 19 wherein the at least one observed property of the library candidate is chosen from the group consisting of color, texture, crystallinity, appearance and odor.

22. A method for changing the operating characteristics of a measurement device, based on a representation of the measurement of a sample, comprising:

the method according to claim 19, and further comprising:

determining the precision state of the representation of the measurement;

determining a quantity related to the determined representation of similarity of the sample to each library candidate; and changing the operating characteristics of the measurement device such that the similarity of a different measurement acquired with the changed operating characteristics to one or more candidates is reduced.

23. A method for changing the operating characteristics of a measurement device, based on a representation of the measurement of a sample, comprising:

the method according to claim 1, and further comprising:

determining the precision state of the representation of the measurement;

determining a quantity related to the determined representation of similarity of the sample to each library candidate; and changing the operating characteristics of the measurement device such that the similarity of a different measurement acquired with the changed operating characteristics to one or more candidates is reduced.

24. A method for determining the most likely composition of a sample, comprising:

obtaining data from a sample, wherein the data comprises a representation of a measured spectrum;

determining a precision state of the representation of the measured spectrum;

providing a plurality of library candidates and, for each library candidate, providing data representing each library candidate, wherein the data comprises a representation of a library spectrum;

determining a representation of the similarity of the sample to a mixture of library candidates using (i) the representation of the measured spectrum; (ii) the precision state of the representation of the measured spectrum; and (iii) the representation of the library spectrum for that library candidate;

determining the most likely composition of the sample based upon the determined representation of similarity of the sample to a mixture of library candidates; and displaying the most likely composition of the sample to a user.

25. A method according to claim 24 wherein the method further comprises:

determining the precision state of the representation of each library spectrum; and determining a representation of the similarity of the sample to a mixture of library candidates using (i) the representation of the measured spectrum; (ii) the precision state of the representation of the measured spectrum; (iii) the representation of the library spectrum for the library candidates; and (iv) the precision state of the representation of the library spectrum for the library candidates.

26. A method according to claim 24 wherein:

the data from the sample further comprises a least one observed property of the sample;

the data for each of at least some of the library candidates further comprises a least one observed property of the library candidate; and determining a representation of the similarity of the sample to a mixture of library candidates using (i) the representation of the measured spectrum; (ii) the precision state of the representation of the measured spectrum; (iii) the representation of the library spectrum for the library candidates; (iv) the at least one observed property of the sample; and (v) the at least one observed property for the library candidates to the extent that there is an observed property for the library candidates.

27. A method according to claim 26 wherein the method further comprises:

determining the precision state of the representation of each library spectrum; and determining a representation of the similarity of the sample to a mixture of library candidates using (i) the representation of the measured spectrum; (ii) the precision state of the representation of the measured spectrum; (iii) the representation of the library spectrum for the library candidates; (vi) the precision state of the representation of the library spectrum for the library candidates;

(v) the at least one observed property of the sample; and (vi) the a least one observed property for the library candidates to the extent that there is an observed property for the library candidates.

28. A method according to claim 24 wherein:

the data from the sample further comprises a least one observed property of the sample;

the data for each of at least some of the library candidates further comprises a least one observed property of the library candidate and a prior probability associated with that observed property of the library candidate; and determining a representation of the similarity of the sample to a mixture of library candidates using (i) the representation of the measured spectrum; (ii) the precision state of the representation of the measured spectrum; (iii) the representation of the library spectrum for the library candidates; (iv) the at least one observed property of the sample; (v) the at least one observed property for the library candidates to the extent that there is an observed property for the library candidates; and (vi) the prior probability associated with that observed property of the library candidates.

29. A method according to claim 28 wherein the method further comprises:

determining the precision state of the representation of each library spectrum; and determining a representation of the similarity of the sample to a mixture of library candidates using (i) the representation of the measured spectrum; (ii) the precision state of the representation of the measured spectrum; (iii) the representation of the library spectrum for that library candidate; (iv) the precision state of the representation of the library spectrum for the library candidates;

(v) the at least one observed property of the sample; (vi) the a least one observed property for the library candidates to the extent that there is an observed property for the library candidates; and (vii) the prior probability associated with that observed property of the library candidates.

30. A method for changing the operating characteristics of a measurement device, based on a representation of the measurement of a sample, comprising:

the method according to claim 24, and further comprising:

determining the precision state of the representation of the measurement;

determining a quantity related to the determined representation of similarity of the sample to the mixture of library candidates; and changing the operating characteristics of the measurement device such that the similarity of a different measurement acquired with the changed operating characteristics to one or more candidates is reduced.

31. A method for determining the most likely classification of a sample, comprising:

obtaining data from a sample, wherein the data comprises a representation of a measured spectrum;

determining a precision state of the representation of the measured spectrum;

providing a plurality of library candidates and, for each library candidate, providing data representing each library candidate, wherein the data comprises a representation of a library spectrum;

wherein the data for each of at least some of the library candidates further comprises the identification of a class to which the library candidate belongs;

determining a representation of the similarity of the sample to each library candidate using (i) the representation of the measured spectrum; (ii) the precision state of the representation of the measured spectrum; and (iii) the representation of the library spectrum for that library candidate;

determining the most likely classification of the sample based upon the determined representation of similarity of the sample to each library candidate; and displaying the most likely classification of the sample to a user.

32. A method according to claim 31 wherein the method further comprises:

determining the precision state of the representation of each library spectrum; and determining a representation of the similarity of the sample to each library candidate using (i) the representation of the measured spectrum; (ii) the precision state of the representation of the measured spectrum; (iii) the representation of the library spectrum for that library candidate; and (iv) the precision state of the representation of the library spectrum for that library candidate.

33. A method for determining the most likely classification of a sample, comprising:

obtaining data from a sample, wherein the data comprises a representation of a measured spectrum;

determining a precision state of the representation of the measured spectrum;

providing a plurality of library candidates and, for each library candidate, providing data representing each library candidate, wherein the data comprises a representation of a library spectrum;

wherein the data for each of at least some of the library candidates further comprises the identification of a class to which the library candidate belongs;

determining a representation of the similarity of the sample to a mixture of library candidates using (i) the representation of the measured spectrum; (ii) the precision state of the representation of the measured spectrum; and (iii) the representation of the library spectrum for that library candidate;

determining the most likely classification of the sample based upon the determined representation of similarity of the sample to a mixture of library candidates; and displaying the most likely classification of the sample to a user.

34. A method according to claim 33 wherein the method further comprises:

determining the precision state of the representation of each library spectrum; and determining a representation of the similarity of the sample to a mixture of library candidates using (i) the representation of the measured spectrum; (ii) the precision state of the representation of the measured spectrum; (iii) the representation of the library spectrum for the library candidates; and (iv) the precision state of the representation of the library spectrum for the library candidates.

35. A system for determining the most likely composition of a sample, comprising:
    apparatus for obtaining data from a sample, wherein the data comprises a representation of a measured spectrum;
    apparatus for determining a precision state of the representation of the measured spectrum;
    apparatus for providing a plurality of library candidates and, for each library candidate, providing data representing each library candidate, wherein the data comprises a representation of a library spectrum;
    apparatus for determining a representation of the similarity of the sample to each library candidate using (i) the representation of the measured spectrum; (ii) the precision state of the representation of the measured spectrum; and (iii) the representation of the library spectrum for that library candidate;
    apparatus for determining the most likely composition of the sample based upon the determined representation of similarity of the sample to each library candidate; and
    apparatus for displaying the most likely composition of the sample to a user.

36. A system according to claim 35 wherein the system further comprises:
    apparatus for determining the precision state of the representation of each library spectrum; and
    apparatus for determining a representation of the similarity of the sample to each library candidate using (i) the representation of the measured spectrum; (ii) the precision state of the representation of the measured spectrum; (iii) the representation of the library spectrum for that library candidate; and (iv) the precision state of the representation of the library spectrum for that library candidate.

37. A system for determining the most likely composition of a sample, comprising:
    apparatus for obtaining data from a sample, wherein the data comprises a representation of a measured spectrum;
    apparatus for determining a precision state of the representation of the measured spectrum;
    apparatus for providing a plurality of library candidates and, for each library candidate, providing data representing each library candidate, wherein the data comprises a representation of a library spectrum;
    apparatus for determining a representation of the similarity of the sample to a mixture of library candidates using (i) the representation of the measured spectrum; (ii) the precision state of the representation of the measured spectrum; and (iii) the representation of the library spectrum for that library candidate;
    apparatus for determining the most likely composition of the sample based upon the determined representation of similarity of the sample to a mixture of library candidates; and
    apparatus for displaying the most likely composition of the sample to a user.

38. A system according to claim 37 wherein the system further comprises:
    apparatus for determining the precision state of the representation of each library spectrum; and
    apparatus for determining a representation of the similarity of the sample to a mixture of library candidates using (i) the representation of the measured spectrum; (ii) the precision state of the representation of the measured spectrum; (iii) the representation of the library spectrum for the library candidates; and (iv) the precision state of the representation of the library spectrum for the library candidates.

39. A system for determining the most likely classification of a sample, comprising:
    apparatus for obtaining data from a sample, wherein the data comprises a representation of a measured spectrum;
    apparatus for determining a precision state of the representation of the measured spectrum;
    apparatus for providing a plurality of library candidates and, for each library candidate, providing data representing each library candidate, wherein the data comprises a representation of a library spectrum;
    wherein the data for each of at least some of the library candidates further comprises the identification of a class to which the library candidate belongs;
    apparatus for determining a representation of the similarity of the sample to a mixture of library candidates using (i) the representation of the measured spectrum; (ii) the precision state of the representation of the measured spectrum; and (iii) the representation of the library spectrum for that library candidate;
    apparatus for determining the most likely classification of the sample based upon the determined representation of similarity of the sample to a mixture of library candidates; and
    apparatus for displaying the most likely classification of the sample to a user.

* * * * *